United States Patent [19]
Morgan

[11] Patent Number: 5,769,637
[45] Date of Patent: Jun. 23, 1998

[54] DENTAL IMPLANT AND ALVEOLAR PROCESS AUGMENTATION STRUCTURES AND METHOD OF INSTALLATION

[75] Inventor: Frank H. Morgan, Las Vegas, Nev.

[73] Assignee: Sofamor Danek Properties, Inc., Memphis, Tenn.

[21] Appl. No.: 647,429

[22] Filed: May 22, 1996

[51] Int. Cl.$^6$ ..................................................... A61C 8/00
[52] U.S. Cl. ............................................................. 433/176
[58] Field of Search ................................... 433/173, 174, 433/175, 176, 201.1; 623/16

[56] References Cited

U.S. PATENT DOCUMENTS

| | | | |
|---|---|---|---|
| 3,739,476 | 6/1973 | Roberts | 433/176 |
| 4,359,318 | 11/1982 | Gittleman | 433/173 |
| 4,516,937 | 5/1985 | Bosker | 433/173 |
| 4,702,697 | 10/1987 | Linkow | 433/176 |
| 4,820,305 | 4/1989 | Harms et al. | 623/16 |
| 5,052,930 | 10/1991 | Lodde et al. | 433/176 |
| 5,201,736 | 4/1993 | Strauss | 433/174 X |
| 5,306,150 | 4/1994 | Gittleman | 433/176 X |
| 5,380,328 | 1/1995 | Morgan | 623/16 |
| 5,513,989 | 5/1996 | Crisio | 433/176 |

*Primary Examiner*—Nicholas D. Lucchesi
*Attorney, Agent, or Firm*—Woodward, Emhardt, Naughton, Moriarty & McNett

[57] ABSTRACT

Prosthetic apparatus for promoting and supporting guided bone tissue regeneration in at least missing or excised portions of the human mandible or maxilla and in bony defects of the mandible and maxilla. The apparatus includes a bone attachment tray formed of tissue-biocompatible titanium sheet material having perforations therethrough for receiving bone screws to affix the tray to stump portions and ridge sections of the mandible or maxilla proximate the missing or excised stump portions or ridge sections and one or more tissue-biocompatible metallic dental tooth root replacement implants which are releasably affixed at one end to the inner surface of the tray and which depend from the tray into the missing or excised portions or bone defects of the mandible or maxilla for incorporation and support in bone tissue regenerated within the tray. The inner surface of the attachment tray may have affixed thereto one or more layers of a biologically and chemically inert microporous membrane sheet material to promote the guided tissue regeneration of replacement bone within the tray and protect the space thereunder from the entry of unwanted bacteria and competitive tissues during the healing and bone regeneration period.

16 Claims, 2 Drawing Sheets

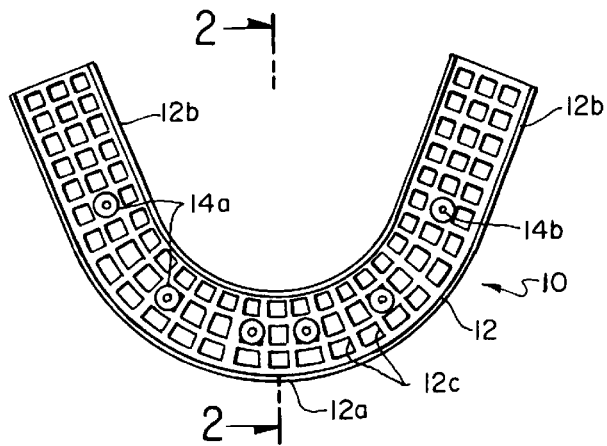
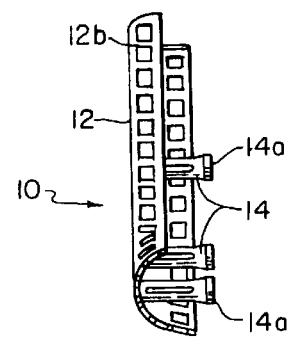
FIG. 1.
FIG. 2.
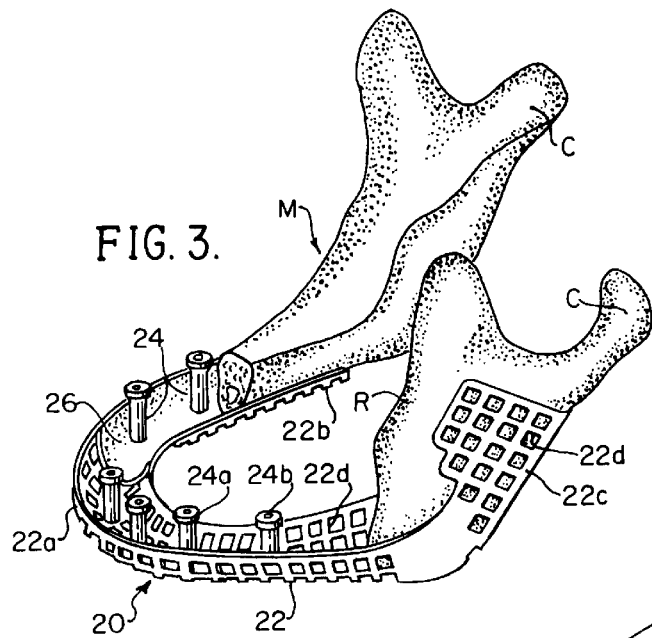
FIG. 3.
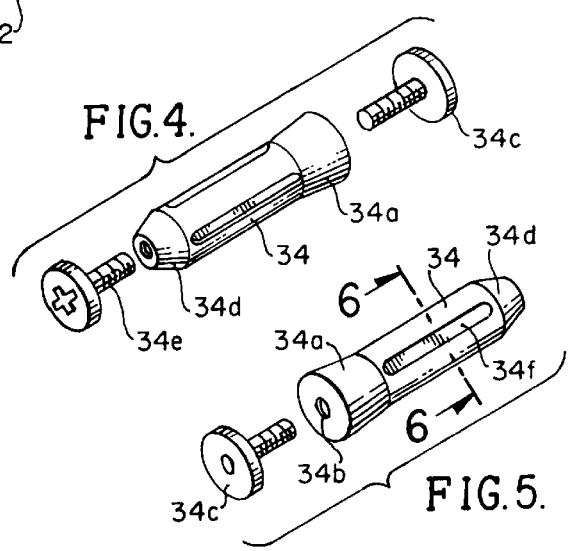
FIG. 4.
FIG. 5.
FIG. 6.

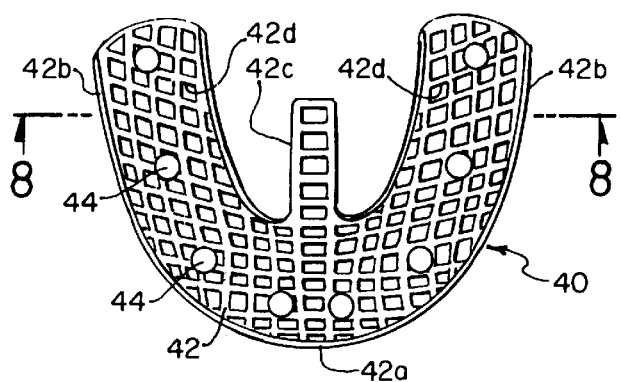
FIG. 7.
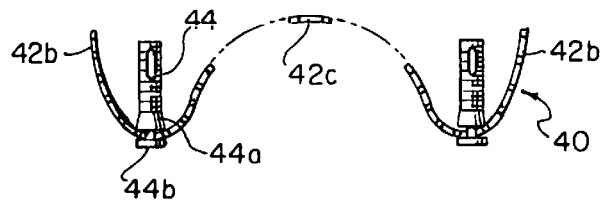
FIG. 8.
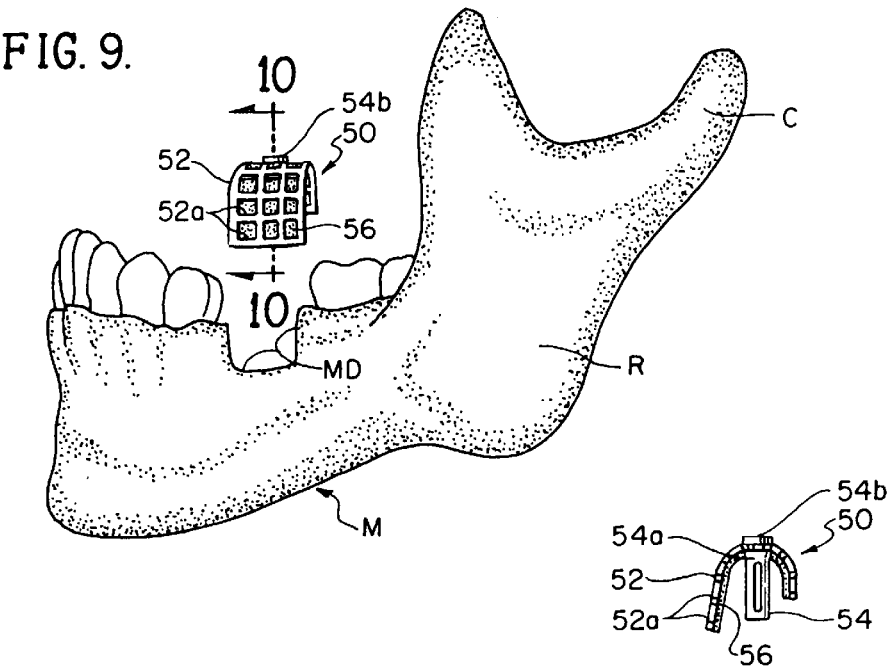

DENTAL IMPLANT AND ALVEOLAR PROCESS AUGMENTATION STRUCTURES AND METHOD OF INSTALLATION

FIELD OF THE INVENTION

The present invention relates to dental implants and alveolar process (or ridge) augmentation structures and methods of installation thereof. More particularly, the invention relates to human artificial tooth root implantation systems and ridge augmentation structures for the guided regeneration of bone in defects of the human maxilla and mandible.

BACKGROUND OF THE INVENTION

During the past 15 years the use of dental implants has become a scientifically accepted treatment concept in dentistry to replace lost or missing teeth in fully or partially edentulous patients. This breakthrough in implant dentistry was initiated 25 years ago by the discovery that post-type implants made of commercially pure titanium could be anchored in the human jawbone with direct contact resulting in the creation of so-called osseointegrated implants. Such implants are characterized by the direct apposition of bone to the surface of titanium implants without evidence of a separating connective tissue layer—the implant interconnected bone having all of the characteristics of normal living bone.

Post-type dental implants have not, however, been successfully applied in reconstructive dentistry where the alveolar process or ridge of the patient's maxilla or mandible includes a large skeletal defect. Such defects in the human facial skeleton can be the result of trauma, infection, congenital pseudoarthrosis, or tumor resection. Thus, in the reconstruction process there is often an initial need to create new bone throughout the defect area. A main hindrance to successful bone healing and for the creation of new bone is the rapid formation of soft connective tissue which may disturb or totally prevent osteogenesis in the defect or a wound area. Numerous methods have been tried and used in an attempt to solve this problem. A most common method involves the harvesting of fresh autogenous bone grafts—an expensive procedure that requires patient hospitalization and the potential risk for donor site morbidity. Other methods have utilized bone powder implants or various commercially available allograft materials. These methods have in general shown little success in solving bone substitution and bone regeneration problems.

Greater bone replacement successes with respect to alveolar process defect reconstruction have resulted from the use of implantable perforated titanium strip and panel structures including partial or full mandible and maxilla cribs or trays which are affixed to mandible and maxilla stubs or stumps via appropriate bone screws. Such biocompatible tray or crib structures, placed under careful reconstructive surgery procedures, are normally packed with bone marrow taken from the patient's hip and covered with soft tissue. After a sufficient healing period, with new bone being generated within the tray or crib, the implanted tray or crib structures may be surgically removed or may remain as part of the reconstructed mandible or maxilla skeletal structure. In either case, the new bone structure of the alveolar process or ridge is frequently adaptable for implanting biocompatible titanium post-type implants as the artificial tooth root structures for completing a full restorative dental plan for the patient.

Another widely used technique for the regeneration of bone associated with bone defects in the alveolar process utilizes the principal of guided tissue regeneration (GTR) developed during the last decade. The technique utilizes a microporous barrier membrane to cover the defect site. The preferred membrane material has taken the form of a biologically and chemically inert ultrafiltration material in sheet form comprised of randomly arranged polytetrafluoroethylene (PTFE) fibers with or without high-density polyethylene backing. Such material is available as "Fluoropore" membrane filter material from the Millipore Corporation or as "Gore-Tex" expanded PTFE barrier material available from W. L. Gore & Associates. The expanded material (e-PTFE) is designed to be cell occlusive even to bacteria. When placed between a bony defect and surrounding connective tissue, these microporous filter materials provide a mechanical barrier to the undesired fast growing soft tissue elements. At the same time, the GTR technique requires that a protective space over the bone defect be maintained for the regeneration and repopulation of the desired but slower developing bone cells.

The guided tissue regeneration process usually takes place in 6–12 weeks and, if properly utilized, can produce impressive bone growth. Barrier membranes may be used at the time of implant placement in areas of an open wall defect around a dental implant or for larger bone defect sites where ridge augmentation may be desired. When the dental surgeon prepares a bony defect site and covers it with a microporous membrane material, it is the goal of the GTR technique (when the membrane material is removed) to find bone growth of sufficient height and/or width to effectively support a dental implant. Unfortunately, in a number of cases collapse or migration of the membrane material has resulted in insufficient bone growth. Tacking of the membrane material at its peripheral edges to adjacent bone structures has been utilized with some success to prevent membrane collapse. For significant bone defects, as where ridge augmentation is indicated and desired, "tenting" of the sheet membrane material to support it above the center of the defect area has helped to prevent collapse.

It is a principal object of the present invention to provide unique dental implant structures for use in the regeneration of healthy bone within bony defects of small and major magnitude in the human maxilla and mandible with such structures providing the concomitant placement of one or more post-type dental implants in the regenerated bone tissue.

It is a further object of the invention to provide unique dental implant structures for reconstructive dentistry which promote guided tissue regeneration within space-protected bony defects in the human maxilla and mandible with such structures providing the concomitant placement of one or more post-type tooth root replacement implants in health bone tissue which has repopulated such defects.

It is a still further object of the invention to provide unique dental implant structures which utilize biocompatible metallic mesh- and grid-type forms shaped for tented placement over maxilla and mandible bone defects and which include one or more biocompatible post-type tooth root replacement units which are to be integrated into new bone tissue which has repopulated such defects.

It is yet another object of the invention to provide unique dental implant structures which utilize biocompatible perforated metallic sheet forms appropriately shaped for surgical placement over large and small bony defects in the human maxilla and mandible and which include microporous membrane sheet material to protect such defects from unwanted cells and connective tissues competitive to bone regeneration and which further include one or more biocompatible post-type metallic implant units for integration into the healthy bone tissue regenerated within such defects.

It is still another object of the invention to provide unique dental implant structures which utilize biocompatible mesh- and grid-type forms of metallic sheet material appropriately contoured for surgical placement over large and small bony defects in the human maxilla and mandible, or as replacement sections of the maxilla and mandible, and which include one or more removably attached biocompatible post-type metallic tooth root replacement implant units for integration into the healthy new bone which has repopulated such bony defects or replacement section of the maxilla and mandible.

It is a further object of the invention to provide a unique method for the regeneration of new replacement bone within defects of the human maxilla and mandible with the concomitant placement of one or more biocompatible metallic post-type tooth root replacement implants within such defects for integration into the new bone tissue which has been regenerated in the defects through practice of the method.

It is a still further object of the invention to provide a unique method for the guided tissue regeneration of new healthy bone within defects of the human maxilla and mandible with the concomitant placement of one or more biocompatible metallic tooth root replacement implants within such defects for integration into the new bone tissue which has been regenerated in the defects through practice of the method.

Other objects and advantages of the invention will be apparent from the following summary and detailed description of the unique dental implant structures of the invention and of the method of reconstructive dentistry practiced via utilization of such implant structures taken together with the accompanying drawing figures.

SUMMARY OF THE INVENTION

The present invention relates to unique combined dental implant and alveolar process (or ridge) augmentation structures and methods for the installation of same with respect to bony defects in the human maxilla and mandible. The invention further relates to the use of such structures to support and promote the technique of guided tissue regeneration (GTR) in large and small bony defects and edentulous spaces in the maxilla and mandible, and within entire excised sections thereof.

In its basic form the unique implant/ridge augmentation structure of the invention comprises a section of biocompatible perforated metallic sheet material contoured or shaped as a tray, cage or crib to cover an edentulous length of maxilla or mandible ridge space which includes a bony defect. The tray, cage or crib (hereinafter referred to simply as a "tray") includes means at each end and periphery to affix the tray to adjacent healthy bone of the ridge. Releasably affixed to the inside of the ridge-contoured tray is one or more post-type biocompatible metallic tooth root replacement implants which extend from the tray (when in fixed position over the bony defect) to a point proximate the bottom of the defect. To promote the rapid regeneration of healthy bone within the defect, and new bone encapsulation of the tooth root replacement implant (or implants) therein, the tray may be packed with bone marrow taken from the patient. After placement the entire tray-implant structure is covered with soft tissue. Alternatively, the inner or outer surface of the tray of the tray-implant structure may carry a layer of microporous membrane sheet material to promote guided tissue regeneration within the bony defect space beneath the tray and protect the defect space from the entry to the space of unwanted bacteria cells and competitive connective tissues during the healing and bone regeneration period.

The preferred perforated metallic sheet material from which the ridge tray is fabricated is commercially pure titanium although trays formed of stainless steel and cobalt-chromium alloys are also acceptable. Such trays may, in fact, be fabricated from mesh- and grid-type panels and sheets of these metallic materials. Pure titanium is preferred because its low density (weight) and elastic modulus (stiffness) are approximately one-half that of stainless steel or cobalt-chromium alloys and the material is corrosion resistant and pliable. Bone trays made from perforated titanium strips and panels can be cut to appropriate configuration and contoured at the time of surgery and, when affixed to healthy bone section with bone screws, provide solid, stable fixation means during trauma and planned reconstructive surgeries. The post-type implants releasably affixed within the trays of the tray-implant structures of the invention are also preferably fabricated of commercially pure titanium.

The unique combined dental implant and alveolar ridge structures of the invention may also take the form of full or partial replacement sections of the maxilla and mandible with the end portions of the structures fastened by bone screws to stubs or stumps of the maxilla or mandible. Such extended length structures will, in accordance with the invention, include a number of post-type dental tooth root replacement implants releasably affixed to the inside surface of the tray portion of the structures and appropriately spaced from one-another for use in later tooth crown restoration procedures (following full healing and bone regeneration of the excised maxilla and/or mandible sections).

The tooth root replacement implants, releasably affixed to the inside of the trays of the tray-implant structures of the invention, are preferably held to the tray by small screws. The heads of such screws may be exposed after full healing and regeneration of bone within such structures with the screws removed to free the implants from the tray. Thus, where removal of the tray is indicated, the implants remain in place within the regenerated bone and provide the implanted bases for the later tooth crown restoration structures. Where biologically and chemically inert microporous membrane sheet material is utilized in association with the tray-implant structures of the invention such sheet material is also remove with the tray.

BRIEF DESCRIPTION OF THE DRAWING FIGURES

FIG. 1 is a top plan view of a full perforated mandibular reconstruction tray structure in accordance with the present invention with inwardly (upwardly) extending (releasably affixed) post-type implants positioned in appropriate spaced relationship along the arcuate length of the tray;

FIG. 2 is a section view of the mandibular tray structure of FIG. 1 taken on line 2—2 of FIG. 1;

FIG. 3 is a perspective skeletal view of a mandibular reconstruction tray structure in accordance with the invention, as applied to a sectioned mandible, the tray being comprised of a mandibular shaped mesh-type metallic plate within which are affixed and appropriately spaced upwardly extending post-type metallic implants, the inner surface of the tray being partially covered with a layer of microporous membrane material;

FIG. 4 is a perspective showing of one possible form of post-type tooth root replacement implant for releasable attachment to the inner surface of a reconstruction tray in accordance with the invention, the implant being viewed from its tray-attachment end with the tray attachment screw forwardly separated therefrom;

FIG. 5 is a reversed perspective showing of the tooth root replacement implant of FIG. 4, the implant being viewed from its crown restoration end with the temporary threaded plug forwardly separated therefrom;

FIG. 6 is a section view of the tooth root replacement implant of FIGS. 4 and 5 taken on line 6—6 of FIG. 5;

FIG. 7 is a top plan view of a full perforated maxillary reconstruction tray structure in accordance with the present invention with inwardly (upwardly) extending (releasably affixed) post-type dental implants positioned in appropriate spaced relationship along the arcuate length of the tray;

FIG. 8 is a section view of the maxillary tray structure of FIG. 7 taken on line 8—8 of FIG. 7;

FIG. 9 is a side skeletal view of a human mandible showing an edentulous area and associated bony defect with a proposed reconstruction tray-implant structure of the invention in upwardly separated position above the edentulous area; and FIG. 10 is a section view of the relatively short mandibular reconstruction tray-implant structure of FIG. 9 taken on line 10—10 of FIG. 9.

DETAILED DESCRIPTION OF THE INVENTION

Referring initially to FIGS. 1 and 2 of the drawings, there is illustrated a full mandibular tray-implant structure 10 in accordance with the present invention. The tray-implant structure 10 basically is comprised of a perforated metallic mandibular reconstruction tray 12 to which a series of post-type tooth root replacement implants 14 have been releasably affixed and project inwardly (upwardly) within the tray. The preferred perforated metallic sheet material from which the tray 12 is fabricated is commercially pure titanium although trays formed of stainless steel and cobalt-chromium alloys are also acceptable. As illustrated in FIGS. 1 and 2, the tray 12 is fabricated from a square mesh panel of pure sheet titanium. Although not visible from the drawing figures, the square perforations of the mesh panel material forming tray 12 are chamfered on the underside of the tray so that the heads of the screws that releasably maintain the post-type implants in their inwardly and upwardly projecting position do not materially project above the surface of the tray material.

The tray 12 extends from its forward mid-point section 12a rearwardly along side portions to its terminal portions 12b. In reconstructive use of the tray-implant structure 10 of the invention, the terminal portions 12b of the tray 12 are affixed by appropriately applied bone screws to rear stump portions of the patients mandible.

The implants 14 may be of a type and configuration as illustrated in FIGS. 3 and 4 and are preferably fabricated of commercially pure titanium. As shown in FIGS. 1 and 2, the implants 14 do not have in place head plug caps which are place in the implants during the mandibular reconstruction healing period. Thus, in these figures the implant head portions 14a are shown (in FIG. 1) to include implant head holes 14b which during the healing period are capped (see the implant plug cap 34c shown in FIGS. 4 and 5). After the healing period the plug caps are removed to open the implant head holes which serve to provide attachment means for the upper tooth restoration structures that are mounted to the implant heads.

In FIG. 3 there is illustrated, in a perspective skeletal view, a full mandibular reconstruction tray-implant structure 20 in accordance with the invention. As shown in the figure, the tray-implant structure 20 is affixed to a human mandible structure M. The remaining portions of the mandible structure M include right and left side ramus sections R and their respective upwardly extending condyles C, substantially the entire forward and side portions of the mandible have been excised because of disease or a traumatic incidence. A perforated metallic mandibular reconstruction tray 22 extends from a rear stump portion of the mandible M on its right side to the ramus section R on the left side of the mandible M. The rear portion 22b of tray 22 is affixed to the right-side stump while the rear portion 22c of the tray is affixed to the left-side ramus by appropriately placed bone screws which extend through tray perforations 22d and into the underlying bone of the stump and ramus portions of the mandible.

In accordance with the present invention post-type tooth root replacement implants 24, appropriately affixed to tray 22 by screws projecting through perforations on the underside of the tray, are placed in spaced series over the arcuate length of the tray. The implants 24 include head portions 24a with threaded head holes 24b which are capped by threaded plugs during the healing period following the installation of the tray-implant structure 20. After the healing period the implant plugs are removed to open the implant head holes 24b which then serve to provide attachment means for the upper tooth restoration structures that are mounted to the implants 24. Further, following the healing and bone regeneration period, surgical decision must be made as to whether or not to remove the tray 22. In the event that it is decided to surgically remove the tray, the screws which affix the implants 24 to the tray are removed so that upon removal of the tray, the implants remain in place within the regenerated mandibular bone for use in the upper tooth restoration procedures.

As shown in FIG. 3, the inner surface of the tray 22 of the tray-implant structure 20 may be covered with a layer of biologically and chemically inert microporous membrane sheet material 26 of the type described hereinbefore. Thus, the membrane material acts to promote guided tissue regeneration of replacement mandibular bone within the tray and protect the tray space from the entry of unwanted bacteria cells and competitive connective tissues during the healing and bone regeneration period. Where removal of the tray is indicated following the healing period, the microporous membrane sheet material is removed with the tray. In some cases the protective sheet of microporous membrane material may be applied to the outer surface of the tray and may be removed separately without the tray following the healing and bone regeneration period.

Referring now to FIGS. 4 and 5 there is shown in perspective views one possible form of post-type tooth root replacement implant that may be used for releasable attachment to the inner surface of a reconstructive tray to form the tray-implant structures of the invention. The implant 34 includes head portion 34a including a threaded head hole 34b. A threaded head cap plug member 34c is shown in separated position in both figures. In FIG. 4 the implant 34 is viewed from its tray attachment end 34d with the tray attachment screw 34e forwardly separated from the implant. FIG. 5 is a reversed perspective showing of the implant 34 viewed from the head end 34a with the temporary cap plug member 34c forwardly separated therefrom. The body of implant 34 includes side grooves 34f which are provided for regenerated bone ingrowth. Such bone ingrowth inhibits future implant rotation in the reconstructed mandible. As previously indicated, the implants, utilized as part of the tray-implant structures of the invention, are preferably formed of commercially pure titanium and they may take a number of forms including that of typical post-type tooth root replacement implants.

FIG. 7 is a top plan view of a full maxillary reconstruction tray-implant structure 40, in accordance with the present invention, including metallic perforated tray 42 bearing inwardly (upwardly) extending (releasably affixed) post-type dental implants 44 positioned in appropriate spaced relationship along the arcuate length of the tray. The tray 42 extends from its forward mid-point section 42a rearwardly along side portions to right and left side terminal portions 42b. The tray 42 also includes a middle perforated strip portion 42c for affixation to the middle bony ridge of the maxilla. The tray 42, with its spaced implants 44, may be affixed to the edentulous maxilla of a patient via appropriate bone screws placed through the tray perforations 42d in spaced orientation along the arcuate edge portions of the tray.

As shown in the FIG. 8 section view of the maxillary tray-implant structure 40 of FIG. 7, taken on line 8—8 of FIG. 7, the post-type dental implants 44 of the structure 40 are releasably affixed at their head ends 44a to tray 42 via screws 44b. As previously indicated, the perforation of the reconstruction trays of the tray-implant structures of the invention are preferably chamfered on their screw affixation side so that the heads of the implant-securing screws do not protrude an appreciable amount over the surface of such trays thereby avoiding harmful or irritating interface with overlying soft tissues. After healing and full bone regeneration within the tray-implant structure 40, the implant attachment screws 44b are removed and the tray portion of the structure may be surgically removed leaving the implants 44 firmly imbedded in the regenerated maxillary bone ridge. The threaded holes (not visible in FIGS. 7 and 8) in the head portions 44a of the implants 44 may thereafter be utilized for the attachment of the upper tooth restoration structures that are mounted to the implant heads.

FIG. 9 is a side skeletal elevation view of the left side of a human mandible M showing an edentulous area and associated bony mandibular defect MD with a proposed reconstruction tray-implant structure 50 of the invention in upwardly separated position above the edentulous area. FIG. 10 is a section view of the relatively short tray-implant structure 50 of FIG. 9 taken on line 10—10 of FIG. 9. The perforated metallic tray 52 of the structure includes an extended-length wall portion on its anterior side (with respect to the downward length wall portion of the tray on its posterior side) so that when the tray is positioned over the defect MD bone screws may be applied through the lower tray perforations 52a and into the mandible to maintain the structure in place enclosing the defect.

Releasably affixed within the tray 52 is a downwardly extending tooth root replacement implant 54 with its head portion 54a held to the underside of tray 52 by a screw 54b. Within the tray is a layer of microporous membrane material 56 so that with the tray-implant structure 50 is fixed in place (tented placement) over the mandibular defect MD, the defect space is secluded and protected for guided tissue regeneration (GTR) of replacement bone within the defect and for the exclusion of bacteria and competing cells from the defect space. Following placement of the tray-implant structure 50 over the defect MD and affixation of the structure to the mandible, a soft tissue flap is established over the structure.

After an appropriate healing period, with bone regeneration within the defect space MD, a soft tissue flap is again developed to expose the tray 52 of the tray-implant structure 50 and the screw 54b to release the implant 54 from the tray. With the bone screws removed from the anterior tray wall, the tray 52 may then be surgically removed (with its inner layer of membrane material) from its position on the regenerated mandible bone area leaving the implant 54 in place within the regenerated mandibular bone. A plug cap is applied to the threaded hole of the implant head and the soft tissue flap is then replaced for further healing of the surgical area. Following a further appropriate healing period, and tooth restoration planning, the implant head is uncovered and the superior tooth restoration is applied.

The invention has been described in connection with a variety of disclosed tray-implant structures utilizing: trays of perforated biocompatible metallic sheet material; inner releasably affixed biocompatible post-type implants; and (where appropriate for guided tissue regeneration) a layer (or layers) of protective microporous membrane material applied to the inner and/or outer surface of the tray. Thus, while the apparatus and methodology of the invention are applicable to reconstructive maxillary and mandibular surgery, correction of maxilla and mandible bone defects, and guided tissue regeneration and enlargement of bone tissue of the human maxilla and mandible, many modifications of the invention will be apparent to those skilled in the art. Accordingly, such modifications are to be included within the spirit and scope of the invention as defined by the following claims.

What I claim is:

1. Prosthetic apparatus for promoting and supporting guided bone tissue regeneration in at least missing or excised portions of the human mandible or maxilla and in bony defects of the mandible or maxilla comprising:

a) a bone attachment tray formed of tissue-biocompatible material having an inner surface and having at least one perforation therethrough for receiving at least one fastener to affix said tray to stump portions and ridge sections of the mandible or maxilla proximate the missing or excised portions or defects thereof; and b) one or more tissue-biocompatible dental tooth root replacement implants releasably affixed at one end to the inner surface of said tray and adapted to depend therefrom into said missing or excised portions or bone defects of the mandible or maxilla for incorporation and support in bone tissue regenerated within said tray; and c) one or more layers of a biologically and chemically inert microporous membrane sheet material affixed to said tray to promote guided tissue regeneration of replacement bone within said tray and protect the space thereunder from entry of unwanted bacteria cells and competitive tissues during the healing and bone regeneration period.

2. Prosthetic apparatus as claimed in claim 1 wherein said microporous membrane sheet material is comprised of randomly dispersed polytetrafluoroethylene fibers and has a pore size range of from about 0.2 to about 3.0 microns.

3. Prosthetic apparatus as claimed in claim 1 wherein said one or more tooth root replacement implants each include a threaded hole in their end affixed to said tray and said one or more implants are each affixed to said tray by a biocompatible threaded fastener extending through a perforation of said tray.

4. Prosthetic apparatus as claimed in claim 1 wherein the bone attachment tray is fabricated from a mesh sheet of commercially pure titanium, said mesh sheet having rows and lines of square or round perforations.

5. Prosthetic apparatus as claimed in claim 4 wherein the perforations of said mesh sheet are chamfered so that the heads of fasteners which may be applied therethrough do not protrude an appreciable amount beyond the surface of said mesh sheet.

6. Prosthetic apparatus as claimed in claim 1 wherein the bone attachment tray extends in arcuate form as an entire artificial mandible and includes end portions for attachment to mandibular bone stubs proximate the ramus portions of the mandible.

7. Prosthetic apparatus as claimed in claim 1 wherein the bone attachment tray is adapted to extend for a length proximate the edentulous space between adjacent natural or artificial teeth of the human mandible or maxilla and includes an extended depending-length portion on its outer side for affixation to healthy bone on the anterior side of the mandible or maxilla.

8. The prosthetic apparatus of claim 1, wherein said tray includes first and second opposed side walls each having at least one perforation therethrough for receiving a bone screw to affix said tray to stump portions and ridge sections of the mandible or maxilla proximate the missing or excised portions or defects thereof.

9. The prosthetic apparatus of claim 1, wherein said tray extends in an arcuate form with a central portion and further includes an affixation strip extending from said central portion, said strip having at least one perforation therethrough for receiving a bone screw.

10. Prosthetic apparatus for promoting and supporting guided bone tissue regeneration in at least missing or excised portions of the human mandible or maxilla and in bony defects of the mandible or maxilla comprising:

a) a bone attachment tray formed of tissue-biocompatible metallic sheet material having at least one perforation therethrough for receiving bone screws to affix said tray to stump portions and ridge sections of the mandible or maxilla proximate the missing or excised portions or defects thereof;

b) one or more tissue-biocompatible metallic post-type dental implants releasably affixed at one end by screw means to the inner surface of said tray and adapted to depend therefrom into the space of said missing or excised portions or bone defects of the mandible or maxilla for incorporation and support in bone tissue regenerated within said tray and said space; and c) one or more layers of a biologically and chemically inert microporous membrane sheet material affixed to the inner surface of said tray to protect the space thereunder from entry of unwanted bacteria cells and competitive tissues during the healing and bone regeneration period within which said apparatus is attached to said mandible or maxilla.

11. Prosthetic apparatus as claimed in claim 10 wherein the bone attachment tray is fabricated from a mesh sheet of commercially pure titanium, said mesh sheet having rows and lines of square or round perforations, and said one or more dental implants are fabricated of commercially pure titanium.

12. Prosthetic apparatus of claim 10, wherein said post-type dental implants includes a second end opposite said one end, said second end defining a cavity therein, and further including a plug member extending into said cavity for removal following bone tissue regeneration within said tray, said cavity in said second end of each of said tooth root replacement implants providing attachment means for upper tooth crown restoration structures to be mounted to said implants following bone tissue regeneration within said tray.

13. Prosthetic apparatus of claim 12, wherein said cavity is threaded and said plug includes mating threads, whereby said plug member is threadedly received in said cavity.

14. The prosthetic apparatus of claim 10, wherein said tray includes first and second opposed side walls each having at least one perforation therethrough for receiving a bone screw to affix said tray to stump portions and ridge sections of the mandible or maxilla proximate the missing or excised portions or defects thereof.

15. The prosthetic apparatus of claim 10, wherein said tray extends in an arcuate form with a central portion and further includes an affixation strip extending from said central portion, said strip having at least one perforation therethrough for receiving a bone screw.

16. A method for promoting and supporting guided bone tissue regeneration in at least missing or excised portions of the human mandible or maxilla and in bony defects of the mandible or maxilla and for the incorporation of tooth root replacement implants in said missing or excised portion of the human mandible or maxilla or bony defects thereof comprising:

a) surgically installing prosthetic apparatus in the space of said missing or excised portions of a human mandible or maxilla or over a bony defect in a human mandible or maxilla, said apparatus comprising: a bone attachment tray formed of tissue-biocompatible metallic sheet material having perforations therethrough for receiving bone screws; and one or more tissue-biocompatible metallic dental tooth root replacement implants affixed at one end by fasteners to the inner surface of said tray and extending therefrom within the tray;

b) fastening said prosthetic apparatus by passing bone screws through the perforations and into healthy bone proximate the ends of the space of said missing or excised portions of said mandible or maxilla or proximate the edge portions of the bony defect in said mandible or maxilla;

c) covering said prosthetic apparatus with a soft tissue flap and maintaining said apparatus in place for the term of an appropriate healing period with the regenerated bone developed within the tray encapsulating and supporting said one or more dental implants affixed to said tray;

d) surgically opening said soft tissue flap at the end of said healing period to expose said tray and removing the fasteners releasably affixing said implants to said tray;

e) surgically removing said tray from the regenerated bone developed within the tray; and f) covering said regenerated bone and said dental implants with said flap for a further healing period.

* * * * *